United States Patent
Pei et al.

(10) Patent No.: US 7,551,961 B1
(45) Date of Patent: Jun. 23, 2009

(54) CARDIAC STIMULATION DEVICE WITH SELECTIVE ATRIAL PACING ON PREMATURE VENTRICULAR COMPLEX DETECTION AND METHOD

(75) Inventors: Xing Pei, Thousand Oaks, CA (US); Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 310 days.

(21) Appl. No.: 11/401,972

(22) Filed: Apr. 10, 2006

(51) Int. Cl.
*A61N 1/39* (2006.01)
(52) U.S. Cl. ......................................................... 607/9
(58) Field of Classification Search ................ 607/9, 607/14, 115
See application file for complete search history.

(56) References Cited

U.S. PATENT DOCUMENTS

| | | | |
|---|---|---|---|
| 4,788,980 A | 12/1988 | Mann et al. | 128/419 |
| 6,292,694 B1 * | 9/2001 | Schloss et al. | 607/9 |
| 6,377,852 B1 | 4/2002 | Bornzin et al. | 607/9 |
| 6,477,419 B2 * | 11/2002 | Levine et al. | 607/14 |
| 6,493,583 B1 * | 12/2002 | Levine et al. | 607/9 |
| 6,498,949 B2 * | 12/2002 | Levine et al. | 607/14 |
| 2003/0208238 A1 * | 11/2003 | Weinberg et al. | 607/9 |
| 2004/0215273 A1 | 10/2004 | Van Bolhuis et al. | 607/27 |

FOREIGN PATENT DOCUMENTS

| | | |
|---|---|---|
| EP | 0 308 535 B1 | 3/1989 |
| EP | 0 536 720 B1 | 4/1993 |

* cited by examiner

*Primary Examiner*—Mark W Bockelman
*Assistant Examiner*—Roland Dinga

(57) ABSTRACT

An implantable cardiac stimulation device provides selective atrial pacing upon detection of a premature ventricular complex (PVC). The device comprises a premature ventricular complex detector that detects premature complexes of the heart, and a sensing circuit that senses atrial events. The device further comprises a P wave discriminator that identifies an atrial event sensed by the sensing circuit following detection of a premature ventricular complex as one of a retrograde P wave and a normal sinus P wave, and an atrial pulse generator that delivers an atrial pacing pulse responsive to the discriminator identifying an atrial event sensed by the sensing circuit following detection of a premature ventricular complex as a retrograde P wave.

12 Claims, 5 Drawing Sheets

CARDIAC STIMULATION DEVICE WITH SELECTIVE ATRIAL PACING ON PREMATURE VENTRICULAR COMPLEX DETECTION AND METHOD

FIELD OF THE INVENTION

This invention relates to an implantable cardiac stimulation device and method for responding to a detected premature ventricular complex (PVC) to prevent a pacemaker mediated tachycardia (PMT). More specifically the present invention relates to such a stimulation device that discriminates between retrograde P waves and sinus P waves before providing atrial pacing to prevent a PMT.

BACKGROUND OF THE INVENTION

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered to be comprised of two major components. One component is a pulse generator which generates the pacing stimulation pulses and includes the electronic circuitry and the power cell or battery. The other component is the lead, or leads, having electrodes which electrically couple the pacemaker to the heart. A lead may provide both unipolar and bipolar pacing and/or sensing electrode configurations. In the unipolar configuration, the pacing stimulation pulses are applied or intrinsic responses are sensed between a single electrode carried by the lead, in electrical contact with the desired heart chamber, and the pulse generator case. The electrode serves as the cathode (negative pole) and the case serves as the anode (positive pole). In the bipolar configuration, the pacing stimulation pulses are applied or intrinsic responses are sensed between a pair of closely spaced electrodes carried by the lead, in electrical contact with the desired heart chamber, with the most proximal electrode serving as the anode and the most distal electrode serving as the cathode.

Pacemakers deliver pacing pulses to the heart to induce a depolarization and a mechanical contraction of that chamber when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses in one chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

Recently, there has been the introduction of pacing systems that stimulate in corresponding chambers of the heart as, for example, the right ventricle (RV) and left ventricle (LV). These are termed biventricular stimulation devices.

Pacemaker Mediated Tachycardia (PMT) also called "endless-loop tachycardia", or "pacemaker reentrant tachycardia", is a recognized pacemaker related rhythm anomaly. PMT can result in any pacemaker capable of sensing and responding to atrial depolarizations when A-V synchrony is dissociated, typically by a premature ventricular complex (PVC). A PVC, as is known, is a native depolarization arising from an ectopic location in the ventricle and occurring early with respect to the next expected conducted ventricular depolarization. Basically, it is an R wave that is not preceded by an atrial event. Such ventricular events may conduct in a retrograde direction to the atria and cause atrial depolarizations. If this atrial depolarization occurs after completion of the PVARP, the device is able to sense this retrograde atrial depolarization, classify it as an alert event, and then, after the appropriate AV delay, delivers a stimulus to the ventricle. Thus, the device provides the anterograde conduction pathway for the reentrant circuit and the intrinsic conduction system of the heart provides the retrograde pathway. A repetitive cycle of ventricular pacing synchronized to the retrograde P-wave can ensue.

Premature ventricular complex (PVC) events are actually the most common trigger for a pacemaker mediated tachycardia (PMT). In the patient whose conduction system can support retrograde conduction, the other prerequisite is that the AV node and atrium be physiologically recovered and hence, not refractory. This occurs when there is AV dissociation. The most common setting for this is the presence of a PVC. In the art, several different methods and hence algorithms, such as extending PVARP, "A pace on PMT" and "A pace on PVC", etc., have been implemented to deal with this inappropriate rhythm disorder. Each method has its unique limitations. In fact, still newer methods and algorithms have been designed to mitigate the limitations of the previous methods and algorithms.

For example, the PVARP extension may simply postpone development of a PMT. In addition, PVARP extensions predispose the heart to sustained loss of atrial tracking when there is intact conduction with a first degree AV block.

The "A pace on PMT" algorithm is intended to terminate a PMT that has already developed. It calls for the intentional delivery of an atrial pacing stimulus after retrograde P-waves are confirmed but at a time when the atrial myocardium should no longer be physiologically refractory. The atrial stimulus will capture the atrium and AV node in the anterograde direction blocking retrograde conduction from the ensuing ventricular paced complex and terminating the PMT.

The "A pace on PVC" algorithm, on the other hand, calls for the delivery of an atrial pacing pulse after a PVC event with the objective of preventing a PMT. An atrial pacing stimulus is delivered after a preset delay when a P-wave (presumed a retrograde P wave) is detected within the PVARP after the PVC event. The atrial stimulus will capture the atrium and AV node in the anterograde direction in order to prevent the PMT from happening. However, the "A pace on PVC" algorithm can create a long short sequence that may initiate another type of tachycardia known as a supraventricular tachycardia.

In one instance, for example, an R-wave was properly detected as a PVC. As a result, an atrial pacing pulse was provided 319 ms after the P-wave (presumed to be a retrograde P wave) according to the "A Pace on PVC" algorithm. While this prevented a PMT, it initiated a non-sustained atrial tachycardia at a cycle length of approximately 270 ms. While the system correctly identified the PVC event, this PVC event was not associated with a retrograde P wave but in fact, a sinus P wave. Had the P wave actually been a retrograde P wave, an undesired intrinsic tachycardia would not have resulted in this case.

Hence, there is a need in the art to improve the specificity of the A-pace on PVC response to insure that the P wave detected after a PVC event is a retrograde P wave. The invention addresses these and other issues.

SUMMARY

What is described herein is an implantable cardiac stimulation device comprising an atrial pulse generator that provides atrial pacing pulses, a premature ventricular complex detector that detects premature ventricular complexes in the heart, and a sensing circuit that senses atrial events. The device further comprises a P wave discriminator that identifies an atrial event sensed by the sensing circuit following detection of a premature ventricular complex as one of a retrograde P wave and a normal sinus P wave. The atrial pulse generator delivers an atrial pacing pulse responsive to the discriminator identifying an atrial event sensed by the sensing circuit following detection of a premature ventricular complex as a retrograde P wave.

The device may further comprise a timer that times atrial event intervals including the atrial event interval completed by the atrial event sensed by the sensing circuit following detection of a premature ventricular complex. The discriminator may include an interval compare that compares the atrial event interval completed by the atrial event sensed by the sensing circuit following detection of the premature ventricular complex to a predetermined interval standard to identify the atrial event sensed by the sensing circuit following detection of a premature ventricular complex as a retrograde P wave or a normal sinus P wave. The predetermined interval standard may be an average P wave to P wave interval. The predetermined interval standard may alternatively be a predicted P wave to P wave interval. The discriminator may identify an atrial event as a retrograde P wave when the atrial event interval completed by the atrial event sensed by the sensing circuit following detection of a premature ventricular complex is shorter than the predetermined interval standard by at least a preset interval difference.

BRIEF DESCRIPTION OF THE DRAWINGS

Further features and advantages of the present invention may be more readily understood by reference to the following description taken in conjunction with the accompanying drawings, in which.

DETAILED DESCRIPTION

The following description includes the best mode presently contemplated for practicing the invention. This description is not to be taken in a limiting sense but is made merely for the purpose of describing the general principles of the invention. The scope of the invention should be ascertained with reference to the issued claims. In the description that follows, like numerals or reference designators will be used to refer to like parts or elements throughout.

Figure 1:
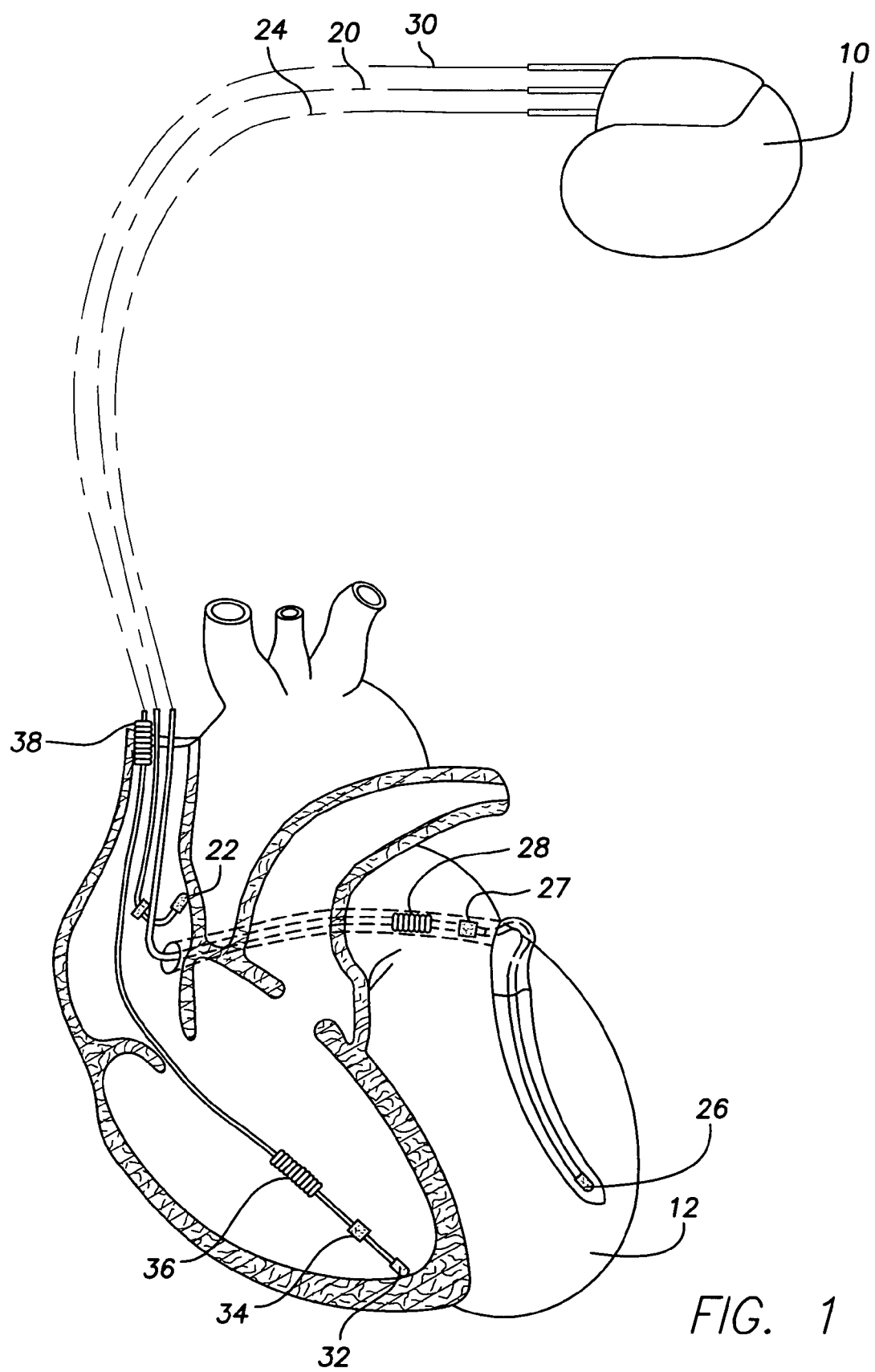
FIG. 1 is a simplified diagram illustrating an implantable stimulation device according to an embodiment of the invention.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
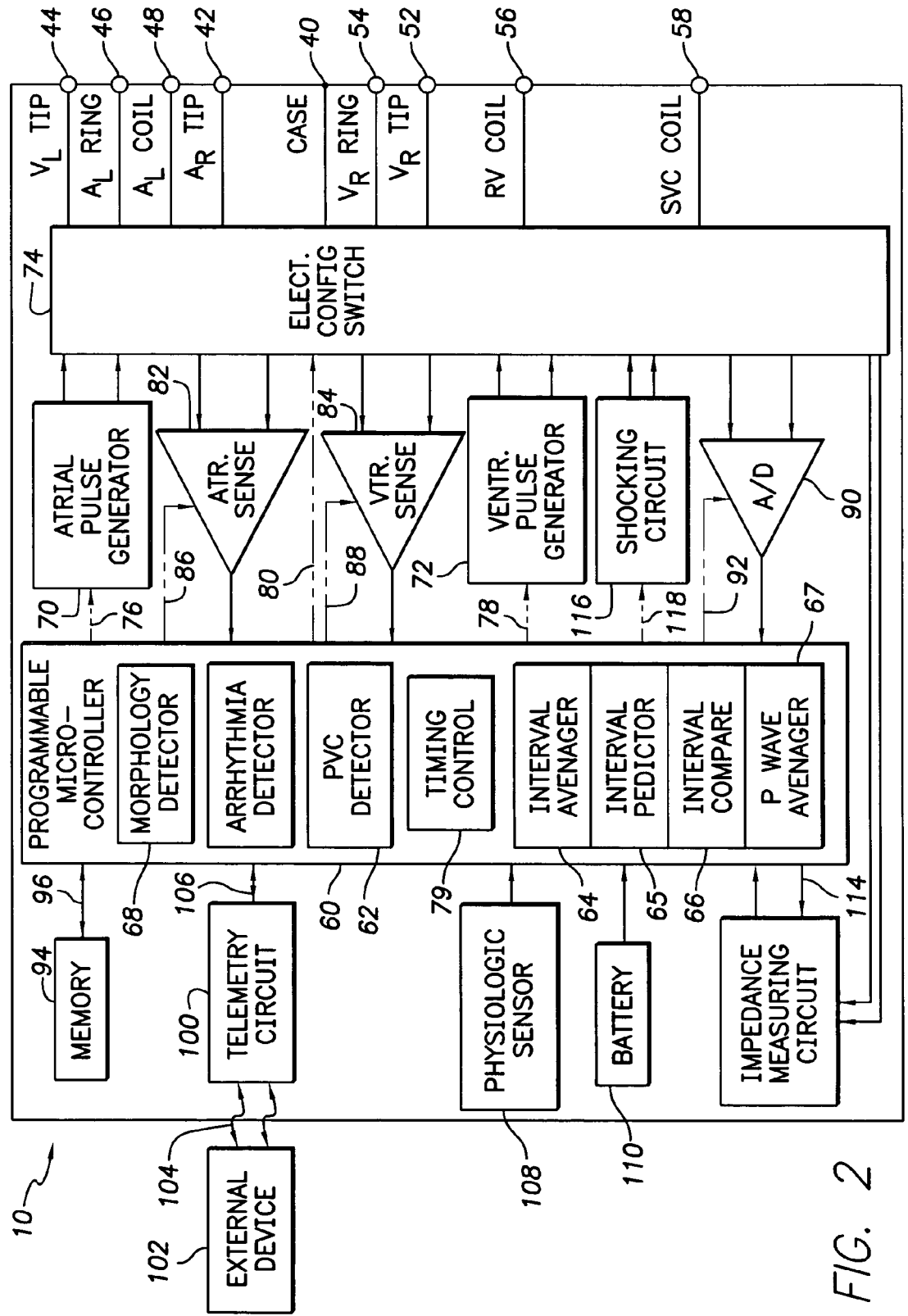
FIG. 2 is a functional block diagram of the implantable stimulation device of FIG. 1 illustrating the basic elements thereof to provide cardioversion, defibrillation and pacing stimulation in four chambers of the heart as well as a PVC response according to an embodiment of the invention.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries, as are known in the art.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

With further reference to FIG. 2, and according to this embodiment, the device further includes a PVC detector 62, an interval averager 64, an interval predictor 65, an interval compare 66, and a P wave morphology averager 67. The PVC detector 62 is provided to detect the occurrence of PVC's. The interval averager 64 is provided to average the P wave to P wave intervals for a number of P wave sinus cardiac cycles. The intervals may be timed by the timing control 79. This average interval then becomes a predetermined interval standard ($T_o$) to which future atrial intervals will be compared to discriminate sinus P waves and retrograde P waves.

Alternatively, the interval predictor 65 is provided to provide a predetermined interval standard ($T_o$) that is a predicted next P wave interval that is dynamically updated for sinus rhythms. Hence, for a steady sinus rhythm, $T_o$ would equal the average. For an increasing sinus rate, $T_o$ would be shorter or equal to the last interval. For a decreasing sinus rate, $T_o$ would be longer than or equal to the last interval. Such interval predicting methods are known in the art.

The interval compare 66 is provided to compare an atrial event interval completed by an atrial event sensed after detection of a PVC to the predetermined interval standard ($T_o$) to identify the atrial event as a sinus P wave or a retrograde P wave. If, for example, the atrial event interval completed by an atrial event sensed after detection of a PVC is less than the predetermined interval standard by at least a preset interval difference, the atrial event is identified as a retrograde P wave. If not, the atrial event is identified as a sinus P wave. Each identification is followed by its own resulting device response.

Figure 4:
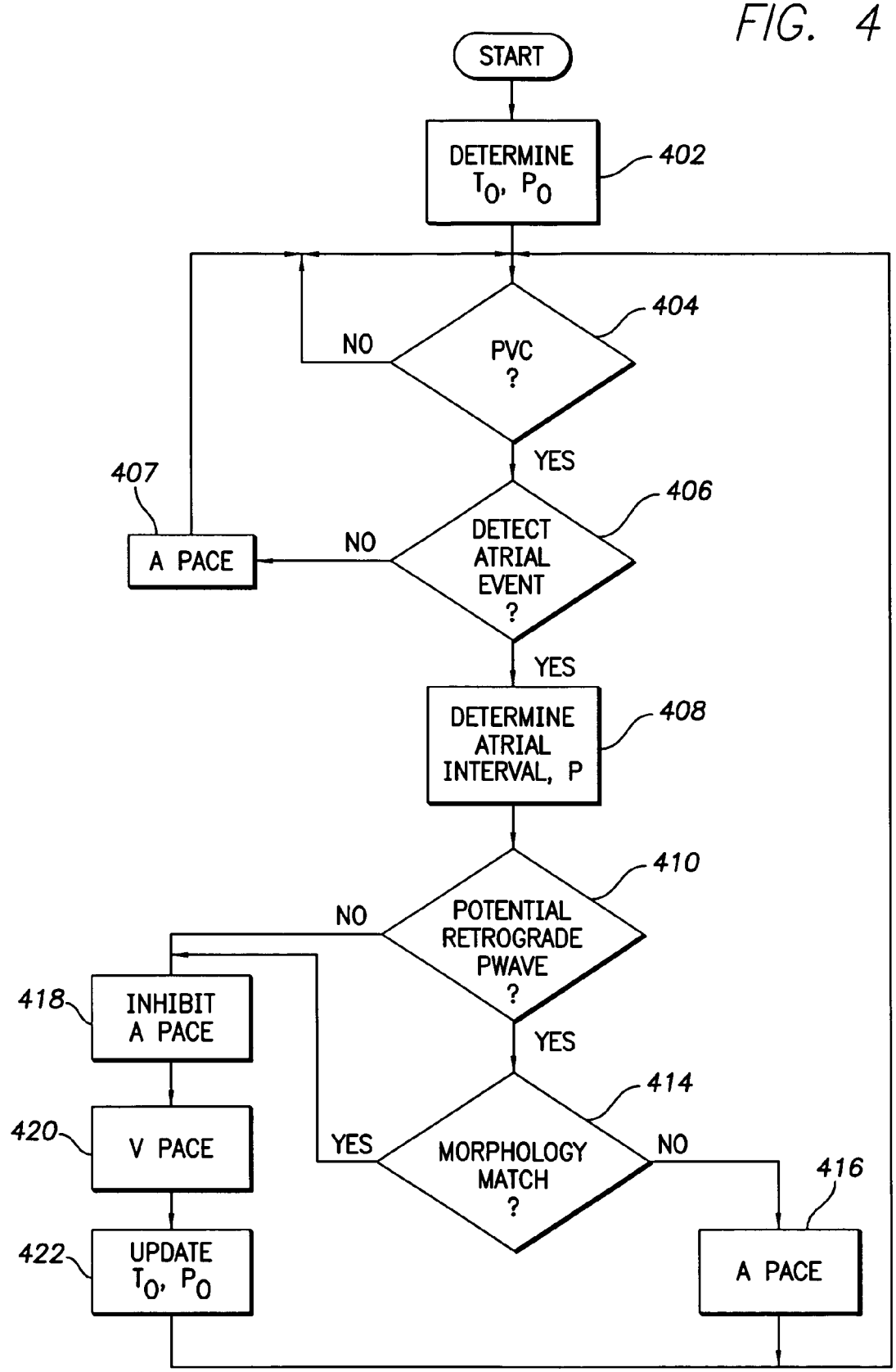
FIG. 4 is a flow chart illustrating an overview of the operation of another embodiment of the present invention wherein P wave discrimination is carried out by timing interval and morphology comparison.
Figure 5:
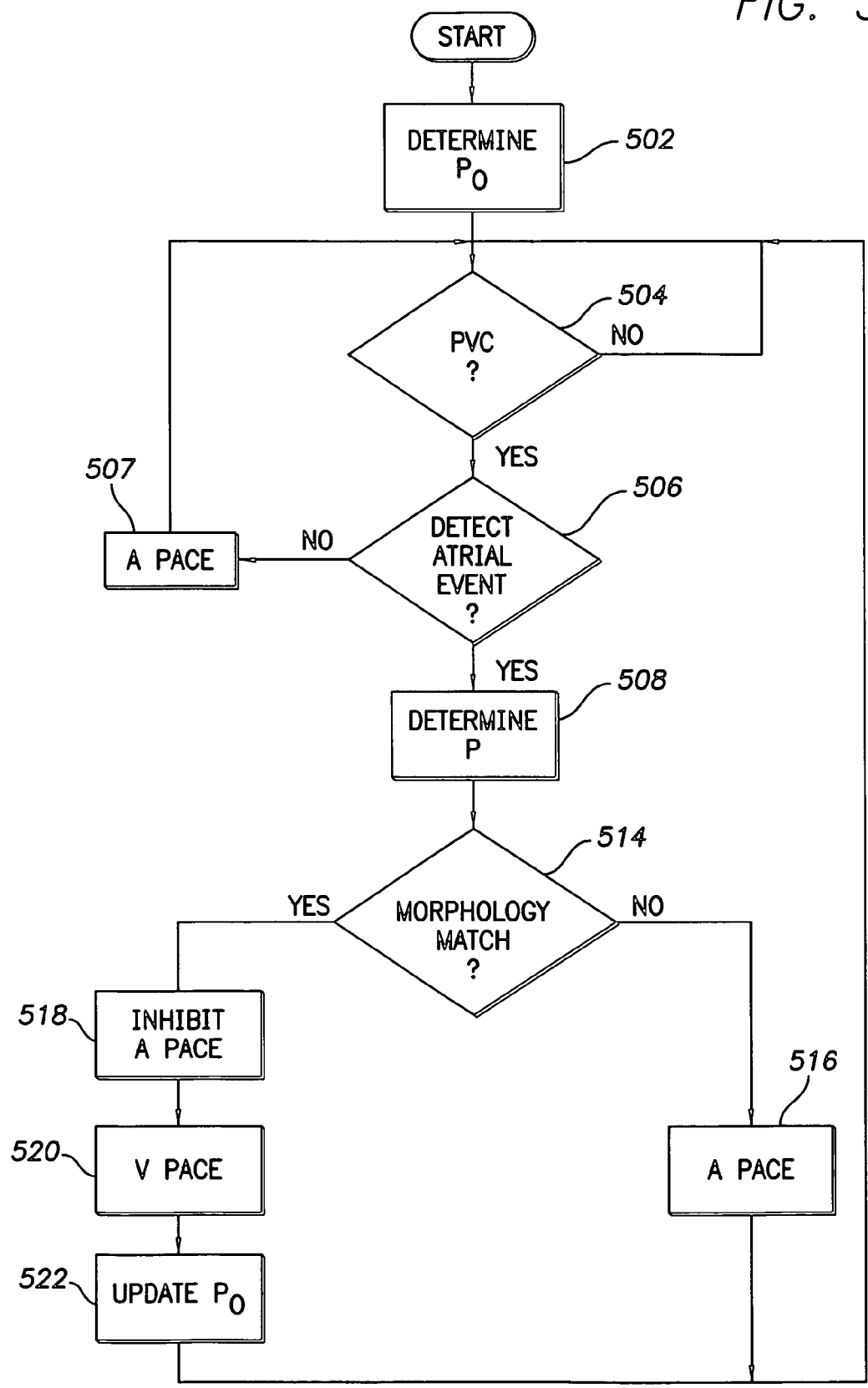
FIG. 5 is a flow chart illustrating an overview of the operation of still another embodiment of the present invention wherein P wave discrimination is carried out by morphology comparison.

The P wave averager 67 is a morphology averager. The morphology detector 68 may be employed to isolate sinus P wave electrograms which are stored in memory 94. When a sufficient number are stored, the P wave averager averages the electrograms to provide a P wave template (Po). The morphology detector 68 may then compare the morphology of an atrial event sensed after detection of a PVC to the P wave morphology template (Po) to identify the atrial event as either a retrograde P wave or sinus P wave. Electrogram template generation and comparison are techniques that are well know in the art. Preferably, the P wave template $P_o$ is updated by each sinus P wave. Further aspects of the embodiments will become apparent as the flow charts of FIGS. 3-5 are described.

Figure 3:
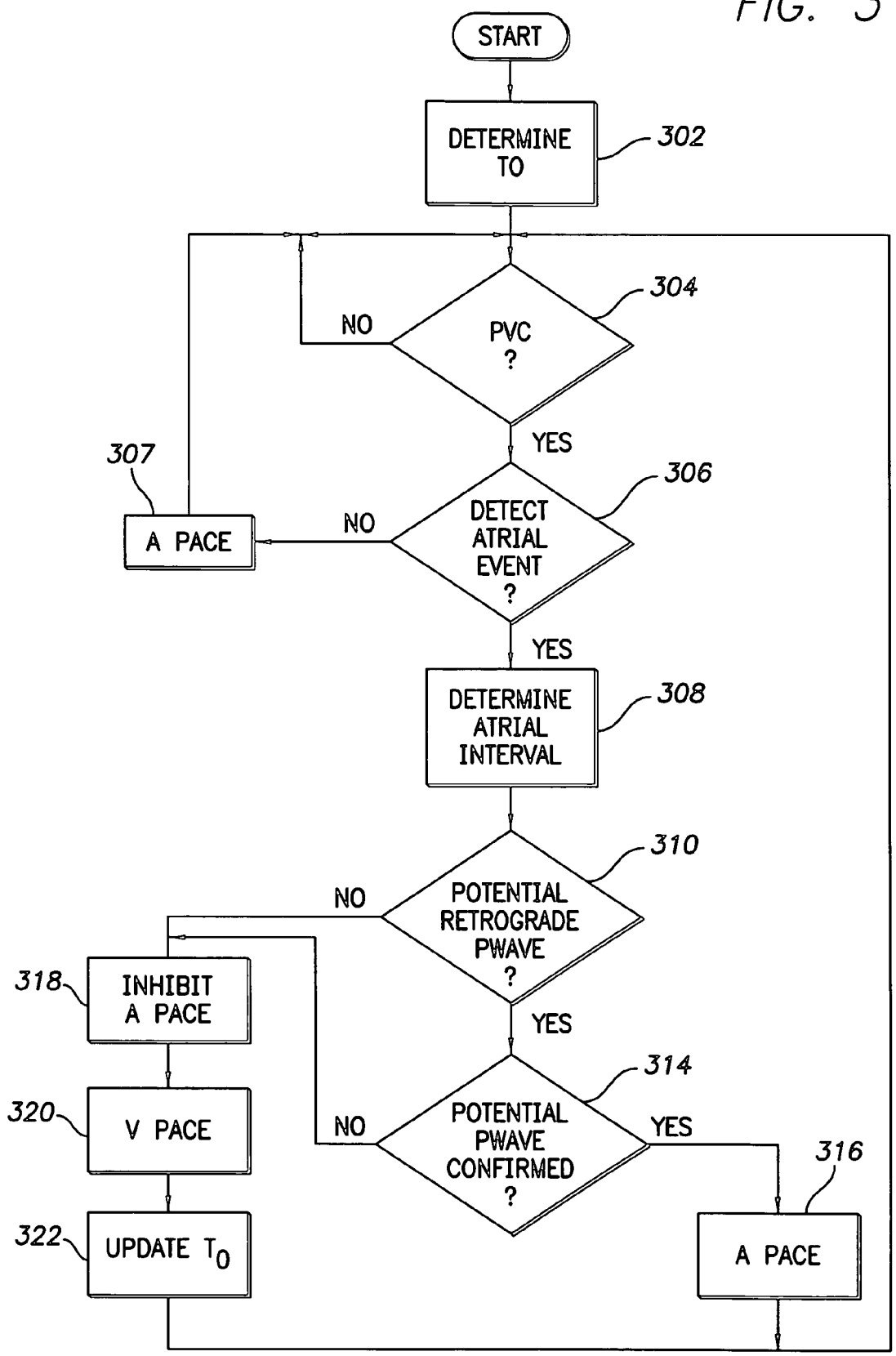
FIG. 3 is a flow chart describing an overview of the operation of one embodiment of the present invention wherein P wave discrimination is carried out by timing interval comparison.

In FIG. 3, a flow chart is shown describing an overview of the operation and novel features implemented in one embodiment of the device 10. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 3 initiates with activity block 302. Here, the predetermined interval standard $T_o$ is determined. The predetermined interval standard $T_o$ may be determined as an average, in a manner as previously described, or a predicted interval, also as previously described.

Next, in decision block 304, it is determined if the PVC detector 62 has detected a PVC. As long as it does not, the process repeatedly returns to decision block 304. However, when a PVC is detected, the process advances to decision block 306 where the device 10 detects for an atrial event. The atrial event may be either a sinus P wave or a retrograde P wave. If an atrial event is not detected, the process proceeds to activity block 307 to deliver an atrial pacing pulse after the PVC atrial escape interval. The process then returns to decision block 304.

The process advances to activity block 308 if atrial event is detected. Here, the timing control 79 determines the length of the atrial interval just completed by the atrial event sensed after the detection of the PVC. The process then moves on to decision block 310. Here, the interval compare 66 compares the interval just completed by the atrial event sensed after the detection of the PVC to the predetermined interval standard $T_o$ determine if the sensed atrial event is potentially a retrograde P wave. Here, $T_o$ may be either the average interval or the predicted interval. In decision block 310 the interval compare 66 determines if the interval difference is less than a predefined threshold and thus is small enough to warrant identifying the atrial event as a sinus P wave. If it is, the process immediately proceeds to activity block 318 to inhibit an atrial pacing response, to activity block 320 to provide a properly timed ventricular pacing pulse, and then to activity block 322 to update the predetermined interval standard $T_o$. The process then returns to decision block 304 for the next PVC detection.

The proper timing of the ventricular pacing pulse would preferably depend on the maximum tracking interval and the AV delay currently set. More specifically, the ventricular pacing pulse is preferably delivered at the last to expire of the AV delay or the maximum tracing interval. This will prevent a cardiac interval considered too short for the patient.

If the difference between the atrial interval just completed by the atrial event sensed after the detection of the PVC and $T_o$ is greater than the predefined threshold, The sensed atrial event is potentially a retrograde P wave and the process moves to decision block 314. Here, it is determined if the interval just completed by the atrial event sensed after the detection of the PVC is longer or shorter than the predetermined interval standard, $T_o$. If it is shorter, the atrial event is confirmed and identified as a retrograde P wave and the process immediately proceeds to activity block 316 where the device provides an atrial pacing response. The atrial pacing response may be, for example, the A pace on PVC, previously referred to or another atrial pacing response. The process then returns to decision block 304.

However, if the atrial interval just completed by the atrial event sensed after the detection of the PVC is longer than the predetermined interval standard, $T_o$, the atrial event is treated as a sinus P wave. Hence, the process then proceeds to activity block 318 to inhibit an atrial pacing response, to activity block 320 to provide a properly timed ventricular pacing pulse, and then to activity block 322 to update the predetermined interval standard $T_o$. The process then returns to decision block 304 for the next PVC detection. Again, the proper timing of the ventricular pacing pulse would preferably depend on the maximum tracking interval and the AV delay currently set. More specifically, the ventricular pacing pulse is preferably delivered at the last to expire of the AV delay or the maximum tracing interval.

FIG. 4 is a flow chart illustrating an overview of the operation of another embodiment of the present invention wherein P wave discrimination is carried out by timing interval and morphology comparison. The process of FIG. 4 initiates with activity block 402. Here, the predetermined interval standard $T_o$ and the P wave template are determined. The predetermined interval standard $T_o$ may again be determined as an average, in a manner as previously described, or a predicted interval, also as previously described. The P wave template may also be determined as previously described.

Next, in decision block 404, it is determined if the PVC detector 62 has detected a PVC. As long as it does not, the process repeatedly returns to decision block 304. However, when a PVC is detected, the process advances to decision block 406 where the device 10 detects for an atrial event. The atrial event may be either a sinus P wave or a retrograde P wave. If an atrial event is not detected, the process proceeds to activity block 407 to deliver an atrial pacing pulse after the PVC atrial escape interval. The process then returns to decision block 404.

The process advances to activity block 408 if an atrial event is detected. Here, the timing control 79 determines the length of the atrial interval just completed by the atrial event sensed after the detection of the PVC and the morphology detector determines the morphology of the sensed atrial event. The process then moves on to decision block 410. Here, the interval compare 66 compares the interval just completed by the atrial event sensed after the detection of the PVC to the predetermined interval standard $T_o$ determine if the sensed atrial event is potentially a retrograde P wave. Again, $T_o$ may be the average interval or the predicted interval. The interval compare 66 determines if the interval difference is less than a predefined threshold and thus is small enough to warrant identifying the atrial event as a sinus P wave. If it is, the process immediately proceeds to activity block 418 to inhibit an atrial pacing response, to activity block 420 to provide a properly timed ventricular pacing pulse, and then to activity block 422 to update the predetermined interval standard $T_o$ and the P wave morphology template. The process then returns to decision block 304 for the next PVC detection.

The proper timing of the ventricular pacing pulse would again preferably depend on the maximum tracking interval and the AV delay currently set. More specifically, the ventricular pacing pulse is preferably delivered at the last to expire of the AV delay or the maximum tracing interval. This will prevent a cardiac interval considered too short for the patient.

If the difference between the atrial interval just completed by the atrial event sensed after the detection of the PVC and $T_o$ is greater than the predefined threshold, the process moves to decision block 414. Here, the morphology detector 68 compares the morphology of the sensed atrial event to the P wave template. If there is a mismatch, the atrial event is confirmed and identified as a retrograde P wave. The process then proceeds to activity block 416 where the device provides an atrial pacing response. The atrial pacing response may be, for example, the A pace on PVC, previously referred to or another atrial pacing response. The process then returns to decision block 404.

However, if the morphology of the atrial event sensed after the detection of the PVC does match the P wave morphology template, the atrial event is confirmed as a sinus P wave. Hence, the process then proceeds to activity block 418 to inhibit an atrial pacing response, to activity block 420 to provide a properly timed ventricular pacing pulse, and then to activity block 422 to update the predetermined interval standard $T_o$ and the P wave morphology template. The process then returns to decision block 404 for the next PVC detection. Again, the proper timing of the ventricular pacing pulse would preferably depend on the maximum tracking interval and the AV delay currently set. More specifically, the ventricular pacing pulse is preferably delivered at the last to expire of the AV delay or the maximum tracing interval.

FIG. 5 is a flow chart illustrating another embodiment of the present invention wherein P wave discrimination is carried out by morphology comparison. The process of FIG. 5 initiates with activity block 502. Here, the P wave template is determined. The P wave morphology template may be derived as previously described.

Next, in decision block 504, it is determined if the PVC detector 62 has detected a PVC. As long as it does not, the process repeatedly returns to decision block 504. However, when a PVC is detected, the process advances to decision block 506 where the device 10 detects for an atrial event. The atrial event may be either a sinus P wave or a retrograde P wave. If an atrial event is not detected, the process proceeds to activity block 507 to deliver an atrial pacing pulse after the PVC atrial escape interval. The process then returns to decision block 504.

The process advances to activity block 508 if an atrial event is detected. Here, the morphology detector determines the morphology of the sensed atrial event. The process then moves to decision block 514. Here, the morphology detector 68 compares the morphology of the sensed atrial event to the P wave template. If there is a mismatch, the atrial event is confirmed and identified as a retrograde P wave. The process then proceeds to activity block 516 where the device provides an atrial pacing response. The atrial pacing response may be, for example, the A pace on PVC, previously referred to or another atrial pacing response. The process then returns to decision block 504.

However, if the morphology of the atrial event sensed after the detection of the PVC does match the P wave morphology template, the atrial event is confirmed as a sinus P wave. Hence, the process then proceeds to activity block 518 to inhibit an atrial pacing response, to activity block 520 to provide a properly timed ventricular pacing pulse, and then to activity block 522 to update the predetermined interval standard $T_o$ and the P wave morphology template. The process then returns to decision block 504 for the next PVC detection. Again, the proper timing of the ventricular pacing pulse would preferably depend on the maximum tracking interval and the AV delay currently set. More specifically, the ventricular pacing pulse is preferably delivered at the last to expire of the AV delay or the maximum tracing interval.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation device comprising:
an atrial pulse generator that provides atrial pacing pulses;
a premature ventricular complex detector that detects premature ventricular complexes of the heart;
a sensing circuit that senses atrial events; and
a P wave discriminator that identifies an atrial event sensed by the sensing circuit following detection of a premature ventricular complex as one of a retrograde P wave and a normal sinus P wave,
the atrial pulse generator being adapted to deliver an atrial pacing pulse responsive to the discriminator identifying an atrial event sensed by the sensing circuit following detection of a premature ventricular complex as a retrograde P wave and
an inhibit circuit that inhibits the atrial pulse generator from providing an atrial pacing pulse responsive to the discriminator failing to identify an atrial event sensed by the sensing circuit following detection of a premature ventricular complex as a retrograde P wave.

2. The device of claim 1, further comprising a timer that times atrial event intervals including the atrial event interval completed by the atrial event sensed by the sensing circuit following detection of a premature ventricular complex and wherein the discriminator includes an interval compare that compares the atrial event interval completed by the atrial event sensed by the sensing circuit following detection of the premature ventricular complex to a predetermined interval standard to identify the atrial event sensed by the sensing circuit following detection of a premature ventricular complex as one of a retrograde P wave and a normal sinus P wave.

3. The device of claim 1, further comprising a morphology detector that determines a morphology of an atrial event sensed by the sensing circuit following detection of a premature ventricular complex and wherein the discriminator includes a morphology compare that compares the morphology of the atrial event sensed by the sensing circuit following detection of a premature ventricular complex to a P wave morphology template to identify the atrial event sensed by the sensing circuit following detection of a premature ventricular complex as one of a retrograde P wave and a normal sinus P wave.

4. The device of claim 3, wherein the P wave template is an average P wave template.

5. The device of claim 1, further comprising and a ventricular pulse generator that delivers a ventricular pacing pulse responsive to the discriminator failing to identify the atrial event sensed by the sensing circuit following detection of a premature ventricular complex as a retrograde P wave.

6. An implantable cardiac stimulation device comprising:
a premature ventricular complex detector that detects premature complexes of the heart;
a sensing circuit that senses atrial events;
a P wave discriminator that identifies an atrial event sensed by the sensing circuit following detection of a premature ventricular complex as one of a retrograde P wave and a normal sinus P wave;
an atrial pulse generator that delivers an atrial pacing pulse responsive to the discriminator identifying the atrial event sensed by the sensing circuit following detection of a premature ventricular complex as a retrograde P wave;
an inhibit circuit that inhibits the atrial pulse generator from providing an atrial pacing pulse responsive to the discriminator failing to identify the atrial event sensed by the sensing circuit following detection of a premature ventricular complex as a retrograde P wave; and
a ventricular pulse generator that delivers a ventricular pacing pulse responsive to the discriminator failing to identify the atrial event sensed by the sensing circuit following detection of a premature ventricular complex as a retrograde P wave.

7. The device of claim 6, further comprising a timer that times atrial event intervals including the atrial event interval completed by the atrial event sensed by the sensing circuit following detection of a premature ventricular complex and wherein the discriminator includes an interval compare that compares the atrial event interval completed by the atrial event sensed by the sensing circuit following detection of a premature ventricular complex to a predetermined interval standard to identify the atrial event sensed by the sensing circuit following detection of a premature ventricular complex as one of a retrograde P wave and a normal sinus P wave.

8. The device of claim 6, wherein the discriminator identifies an atrial event as a retrograde P wave when the atrial event interval completed by the atrial event sensed by the sensing circuit following detection of a premature ventricular complex is shorter than the predetermined interval standard by at least a preset interval difference.

9. The device of claim 6, further comprising a morphology detector that determines a morphology of the atrial event sensed by the sensing circuit following detection of a premature ventricular complex and wherein the discriminator includes a morphology compare that compares the morphology of the atrial event sensed by the sensing circuit following detection of a premature ventricular complex to a P wave morphology template to identify the atrial event sensed by the sensing circuit following detection of a premature ventricular complex as one of a retrograde P wave and a normal sinus P wave.

10. The device of claim 6, wherein the ventricular pulse generator delivers the ventricular pacing pulse an AV delay after the atrial event sensed by the sensing circuit following detection of the premature ventricular complex.

11. The device of claim 6, wherein the ventricular pulse generator delivers the ventricular pacing pulse at the end of a maximum tracking rate interval.

12. The device of claim 6, wherein the ventricular pulse generator delivers the ventricular pacing pulse at the latest to end of one of a maximum tracking rate interval and an AV delay.

\* \* \* \* \*